US008457705B2

(12) United States Patent
Shoureshi et al.

(10) Patent No.: US 8,457,705 B2
(45) Date of Patent: Jun. 4, 2013

(54) BRAIN IMAGING SYSTEM AND METHODS FOR DIRECT PROSTHESIS CONTROL

(75) Inventors: Rahmat A. Shoureshi, Golden, CO (US); Christopher M. Aasted, Broomfield, CO (US)

(73) Assignee: University of Denver, Denver, CO (US)

( * ) Notice: Subject to any disclaimer, the term of this patent is extended or adjusted under 35 U.S.C. 154(b) by 780 days.

(21) Appl. No.: 12/447,428

(22) PCT Filed: Oct. 24, 2007

(86) PCT No.: PCT/US2007/082410
§ 371 (c)(1),
(2), (4) Date: Aug. 3, 2009

(87) PCT Pub. No.: WO2008/052070
PCT Pub. Date: May 2, 2008

(65) Prior Publication Data
US 2010/0191079 A1    Jul. 29, 2010

Related U.S. Application Data

(60) Provisional application No. 60/862,862, filed on Oct. 25, 2006.

(51) Int. Cl.
*A61B 5/1455* (2006.01)
*A61B 5/04* (2006.01)

(52) U.S. Cl.
USPC ............... 600/323; 600/546; 607/53; 607/54

(58) Field of Classification Search
USPC .................................. 600/323, 476
See application file for complete search history.

(56) References Cited

U.S. PATENT DOCUMENTS

| 5,730,146 | A | | 3/1998 | Itil et al. |
|---|---|---|---|---|
| 5,782,755 | A | * | 7/1998 | Chance et al. ............... 600/322 |
| 5,807,263 | A | * | 9/1998 | Chance ......................... 600/476 |
| 5,853,370 | A | * | 12/1998 | Chance et al. ............... 600/473 |
| 5,995,857 | A | * | 11/1999 | Toomim et al. ............... 600/322 |
| 6,223,069 | B1 | * | 4/2001 | Pfeiffer et al. ............... 600/431 |
| 6,349,293 | B1 | * | 2/2002 | Yamaguchi ..................... 706/2 |
| 6,904,302 | B2 | | 6/2005 | Hirabayashi et al. |
| 7,047,149 | B1 | | 5/2006 | Maki et al. |

(Continued)

OTHER PUBLICATIONS

Schwartz et Al., "Brain-Controlled Interfaces: Movement Restoration with Neural Prosthetics", Neuron vol. 52, Issue 1, pp. 205-220, Oct. 5, 2006.*

(Continued)

*Primary Examiner* — Clayton E Laballe
*Assistant Examiner* — Kevin Butler
(74) *Attorney, Agent, or Firm* — Kilpatrick Townsend & Stockton, LLP

(57) ABSTRACT

Methods and systems for controlling a prosthesis using a brain imager that images a localized portion of the brain are provided according to one embodiment of the invention. The brain imager provides motor cortex activation data by illuminating the motor cortex with near infrared light (NIR) and detecting the spectral changes of the NIR light as passes through the brain. These spectral changes can be correlated with brain activity related to limbic control and may be provided to a neural network, for example, a fuzzy neural network that maps brain activity data to limbic control data. The limbic control data may then be used to control a prosthetic limb. Other embodiments of the invention include fiber optics that provide light to and receive light from the surface of the scalp through hair.

23 Claims, 17 Drawing Sheets

U.S. PATENT DOCUMENTS

| | | | |
|---|---|---|---|
| 7,280,859 B2 * | 10/2007 | Maki et al. | 600/344 |
| 7,386,335 B2 * | 6/2008 | Eda et al. | 600/323 |
| 7,398,255 B2 * | 7/2008 | Lauer et al. | 706/8 |
| 7,610,082 B2 * | 10/2009 | Chance | 600/475 |
| 7,983,741 B2 * | 7/2011 | Chance | 600/476 |
| 8,260,428 B2 * | 9/2012 | Fink et al. | 607/54 |
| 2005/0228291 A1 * | 10/2005 | Chance | 600/476 |
| 2008/0139908 A1 * | 6/2008 | Kurth | 600/340 |
| 2008/0262327 A1 * | 10/2008 | Kato | 600/324 |
| 2010/0016732 A1 * | 1/2010 | Wells et al. | 600/476 |
| 2011/0208675 A1 | 8/2011 | Shoureshi et al. | |

OTHER PUBLICATIONS

Petrosyuk Iryna, Neuro-fuzzy Model for Image Processing in Electro-optical Applications Lviv-Slavsko, Modern Problems of Radio Engineering, Telecommunications, and Computer Science, 2006. TCSET 2006. International Conference, Nat. Tech. Univ. of Ukraine, Kyiv, pp. 218-221, Feb. 28-Mar. 4, 2006.*

Tomohiro Takagi et Al., Fuzzy Identification of Systems and Its Applications to Modeling and Control, IEEE Transactions on Systems, Man, and Cybernetics, vol. 15, No. 1, Jan./Feb. 1985.*

International Application No. PCT/US2007/082410, International Search Repor and Written Opinion, 8 Pages, Jul. 1, 2008.*

Shih JJ et Al., Brain-Computer interfaces in Medicine, Mayo Foundation for Medical Education and Research, Elsevier Inc., Department of Neurology, Mayo Clinic, Jacksonville Florida, 2012 abstract.*

Francis H. Y. Chan et al., Fuzzy EMG Classification for Prosthesis Control, EEE Transactions of Rehabilitation Engineering, vol. 8 No. 3, Sep. 2000.*

International Application No. PCT/US2007/082410, International Search Report and Written Opinion, 8 pages, Jul. 1, 2008.

Craelius, William, "The Bionic Man: Restoring Mobility," Science, vol. 295, pp. 1018-1019, 1021, Feb. 8, 2002.

Schwartz, Andrew B. et al., "Brain-Controlled Interfaces: Movement Restoration With Neural Prosthetics," J. Neuron, vol. 52, Issue 1, pp. 205-220, Oct. 5, 2006.

Shoureshi, Rahmat A. et al., "Auto-Adaptive Human Interface for Direct Brain Control of Artificial Limbs," Proceedings of the FOSBE 2007, pp. 385-390, Sep. 9-12, 2007.

Tabuchi, Hiroko, "Hitachi: Move the Train With Your Brain," Associated Press, 2 pages, Jun. 22, 2007.

WTEC, "Report on North American and European BCI Research," WTEC Workshop on Brain Computer Interface Research, 10 pages, Jul. 21, 2006.

Author Unknown, "Direct Brain Control of Artificial Limb Using an Integrated Sensory System of Electroencephalography. Electromyography, and Near-Infrared Spectroscopy," Aasted-NIH Grant Proposal, 2009, 15 pages, USA.

* cited by examiner

BRAIN IMAGING SYSTEM AND METHODS FOR DIRECT PROSTHESIS CONTROL

CROSS-REFERENCES TO RELATED APPLICATIONS

This application is a national stage of International Application No. PCT/US2007/082410, with an international filing date of Oct. 24, 2007, which claims the benefit, of commonly assigned U.S. Provisional Application No. 60/862,862, filed Oct. 25, 2006, entitled "A Brain Imaging System and Method for Providing Direct Brain Control of Prostheses, Artificial Limbs and Robotic Systems Using Near Infrared Optical Imaging," the entirety of which is herein incorporated by reference for all purposes.

This disclosure relates in general to prosthesis control and, but not by way of limitation, to a prosthesis using a brain imaging system amongst other things.

BACKGROUND

The statistics for limb loss are sobering. Approximately 2 million people in the United States suffer from limb loss. Each year more than 185,000 amputations occur in the United States. It is estimated that one out of every 200 people in the U.S. has had an amputation. The statistics for limb loss in developing countries are even more troubling. Worldwide it is estimated that 650,000 people suffer from upper-extremity limb loss.

Many prosthetic limbs are currently controlled by electromyography (EMG) and are referred to as myoelectric prostheses. Electromyography monitors the electric potential of flexor and extensor muscles in the remaining portion of the limb. Using the differential between the flexor and extensor muscles potential, it can be determined whether to close or open a prosthetic hand. This system requires the user to consciously flex and relax muscles in order to control the artificial hand, because the activity of the remaining muscles would have normally controlled a different movement within the limb than the output of the prosthesis.

Other prostheses are actuated using mechanical and/or biosensors. Biosensors detect signals from the user's nervous or muscular systems, which is relayed to a controller located inside the device. Limbic and actuator feedback may be used as inputs to the function of the controller. Mechanical sensors process aspects affecting the device (e.g., limb position, applied force, load) and relay this information to the biosensor or controller, for example force meters and accelerometers. A prosthesis controller may be connected to the user's nervous and muscular systems as well as to the prosthesis itself. The controller may send intention commands from the user to the actuators of the device, and may interpret feedback from the mechanical and biosensors to the user.

Primary motor function of human muscles is directed within the motor cortex of the brain. The primary motor cortex is responsible for motion execution and the premotor cortex is responsible for motor guidance of movement and control of proximal and trunk muscles. While sections of the motor cortex are relatively well mapped to muscles and/or muscle groups, understanding brain activity within such sections of the motor cortex is not well established. Previous attempts of brain imaging have typically focused on large portions of the brain to map general zones of the brain to general functions.

BRIEF SUMMARY

A method for controlling a prosthesis is provided according to one embodiment of the invention. The method includes receiving a plurality of input signals from a brain imager, such as a NIR brain imager. The input signals may correspond to brain activity at one or more portions of the motor cortex. A neural network, such as a fuzzy neural network, may then be used to map the plurality of input signals to a plurality of output signals. The neural network may be trained to map an input signal associated with the one or more portions of the motor cortex to an output signal that corresponds with one or more muscle groups The output signals may then be provided to a prosthesis, wherein the prosthesis is configured to respond to the output signals. The method may also include illuminating light on a portion of the brain using one or more light sources and receiving a plurality of light signals at the surface of the scalp using a plurality of photodiodes. The light sources may include LEDs, fiber optics and/or lasers. Detected light may have traveled from the one or more light sources through a plurality of sub-portions of the brain and may be detected at the plurality of photodiodes. This detected light may then be provided as a plurality of input signals.

A prosthesis control system that includes a brain imager is provided according to another embodiment of the invention. The system includes one or more light sources, a plurality of photodiodes, a controller and a prosthesis. The one or more light sources are configured to irradiate light into a first portion of the brain, such as the motor cortex. The light sources may include LEDs, lasers and/or fiber optics. The light may be near infrared light. The plurality of photodiodes may be configured to detect a portion of the light transmitted into the first portion of the brain. The photodiodes may receive light from the scalp through a fiber optic. The detected light may travel at least from the one or more light sources through a plurality of sub-portions of the brain and be detected at the plurality of photodiodes. The controller may be configured to receive a plurality of inputs from the plurality of photodiodes. The controller may perform a plurality of functions. For example, the controller may determine the relative concentration of oxy-hemoglobin and/or deoxy-hemoglobin within the first portion of the brain from the plurality of photodiode inputs. The controller may determine the brain activity at a plurality of sub-portions of the first portion of the brain from the relative concentrations of oxy-hemoglobin and hemoglobin. The controller may also determine a plurality of limbic control signals from the brain activity within the first portion of the brain. The prosthesis may be configured to receive the limbic control signals from the controller and configured to operate in response to the limbic control signals. The controller may include a neural network inference engine that is configured to determine the plurality of limbic control signals from the brain activity within a first portion of the brain. The system may also include a headset with photodiodes, fiber optics and/or light sources embedded therein.

A fiber optic for transmitting light into the brain through the scalp and past hair is provided according to another embodiment of the invention. The fiber optic includes an optical fiber and a bulb. The optical fiber includes a distal end, a proximal end and elongated fiber body. The proximal end is configured to receive light from a light source and the elongated fiber body is configured to channel light received from the light source at the proximal end to the distal end. The bulb is coupled with the distal end of the optical fiber. The bulb is configured to transmit light from the elongated fiber optic body into the brain through the scalp and past hair. The bulb may be substantially spherically shaped, that is, the bulb may be a sphere, spheroid, hemispherical, oblong, oval, etc. The bulb may also comprise a hemisphere. The optical fiber and bulb may comprise the same material and may be fused together.

A method for training a prosthesis system is disclosed according to another embodiment of the invention. The prosthesis system may include a neural network, a brain imaging system and a prosthesis. The training may utilize an electromyograph. The method may include receiving brain activity data from the brain imaging system, receiving muscular response data from the electromyograph, wherein the muscular response data corresponds with the brain activity, and training the neural network to produce the muscular response data from the brain activity data.

DETAILED DESCRIPTION OF THE INVENTION

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

One embodiment of the invention provides for various systems and methods for providing prosthetic control using a brain imager. For example, according to one embodiment of the invention, a near infrared (NIR) brain imager is configured to detect motor cortex activation specifically at a portion of the motor cortex corresponding with a specific muscle or muscle group. This motor cortex activation data may then be translated into limbic control signals using a neural network, for example, a fuzzy neural network, and then used to actuate an artificial limb. A fuzzy neural network is provided that quickly learns limbic actuation outputs from brain activation data according to another embodiment of the invention. As another example, a fiber optic is provided that may be used to transmit light into and/or receive light from the brain. Various other embodiments will be described throughout the body of this disclosure.

This disclosure provides a description of various embodiments of the invention and is organized as follows: First, a brain imager that provides noninvasive localized brain activity data is described according to one embodiment of the invention is disclosed. A specific example of such a brain imager, a NIR brain imager, is then presented according to one embodiment of the invention along with a description of its operation using the Beer-Lambert Law. A neuro-fuzzy inference engine is described, according to another embodiment of the invention, that provides learned limbic outputs from brain activity inputs. A training system according to another embodiment of the invention is then described that may be used to associate specific brain activity with specific limbic outputs. Fiber optic sensor and/or detectors are disclosed according to another embodiment of the invention. Finally, a system that employs a brain imager and neural network to control an artificial limb is disclosed.

I. Brain Imager

Figure 1:
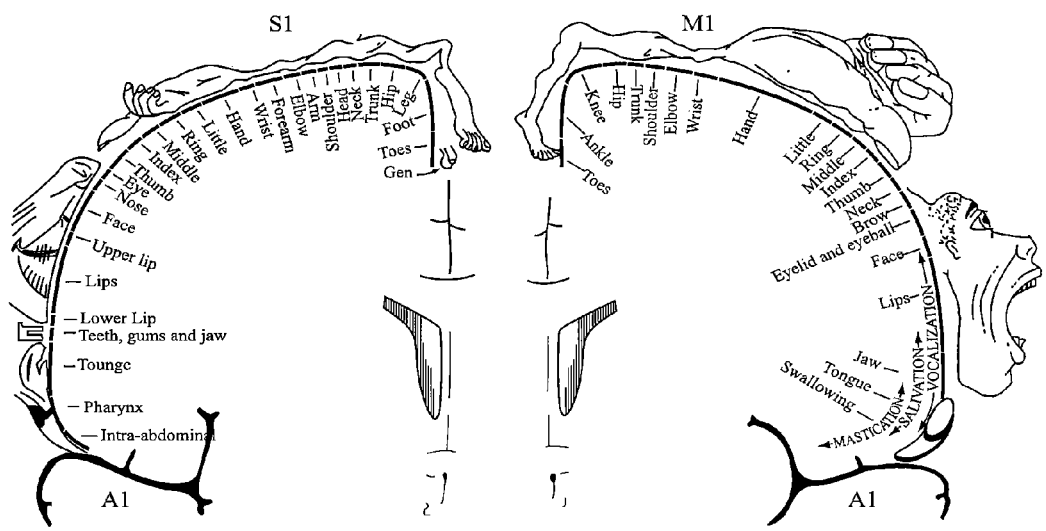
FIG. 1 shows a homunculus of the human brain showing the relative areas and size of portions of the motor cortex that are used for limbic control.

There is a precise somatotopic representation of the different body parts in the primary motor cortex, as shown by the motor homunculus in FIG. 1. The arm and hand motor cortex is the largest, and lies between the leg and face area. The lateral area of the primary motor cortex is arranged from top to bottom in areas that correspond to the buttocks, torso, shoulders, elbows, wrists, fingers, thumbs, eyelids, lips and jaw. Interior sections of the motor area folding into the medial longitudinal fissure correspond with the legs. Different portions of the motor cortex are activated during control of specific portions of the body.

A brain imager configured to provide noninvasive brain activity data from a select portion of the brain is provided according to one embodiment of the invention. The brain imager, for example, may utilize light to detect indications of brain activity within a select portion of the motor cortex. This brain activity may correspond with a specific motor function. For example, the brain imager may only monitor the portion of the brain that is used to control, for example, the forearm, ankle, shoulder, wrist, leg, hand, hip, or foot, etc. In one embodiment of the invention, the brain imager provides localized brain activity detection over only the specific portion of the brain that is associated with a specific motor function.

Figure 2A:
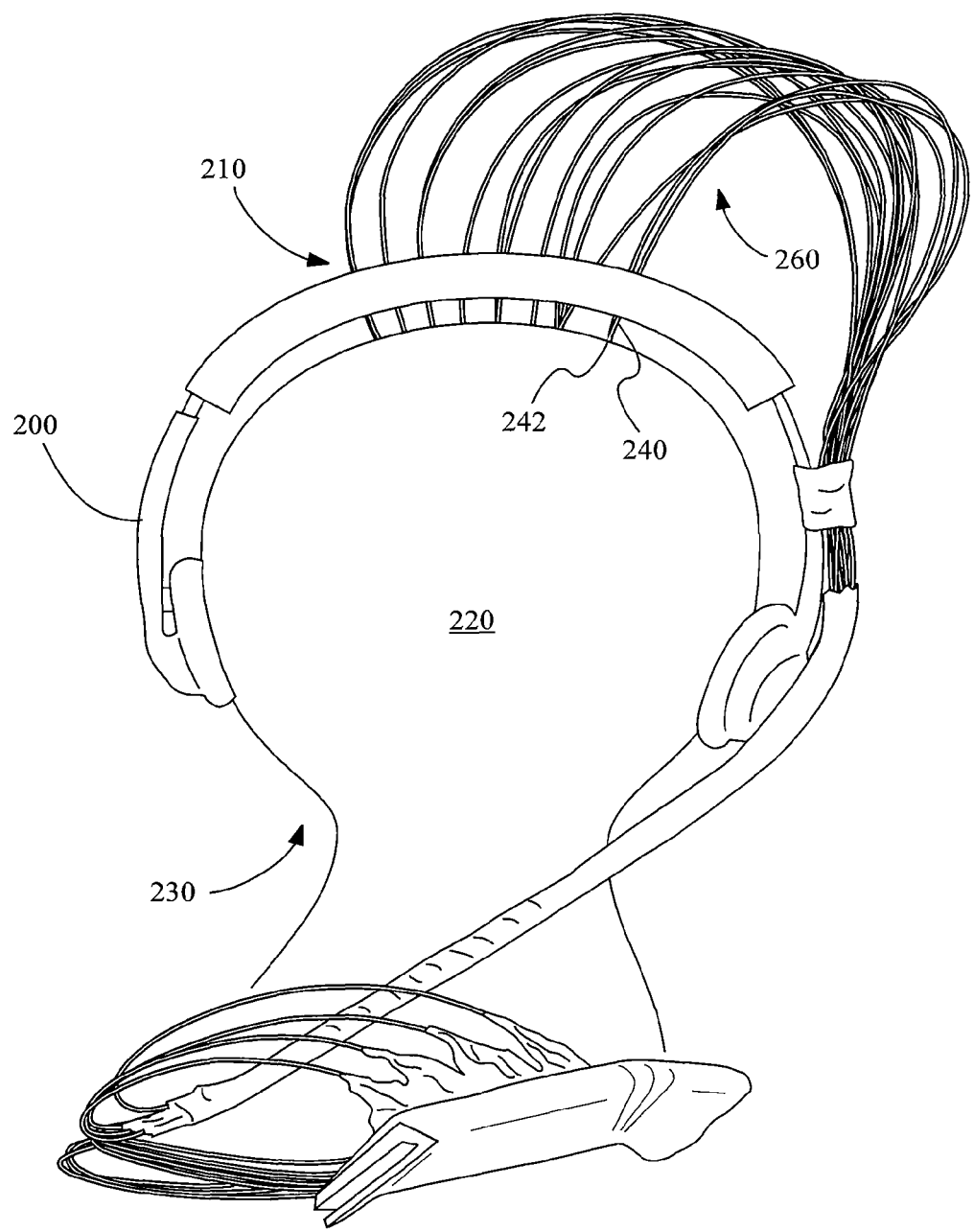
FIG. 2A shows a brain imaging headset according to one embodiment of the invention.
Figure 2B:
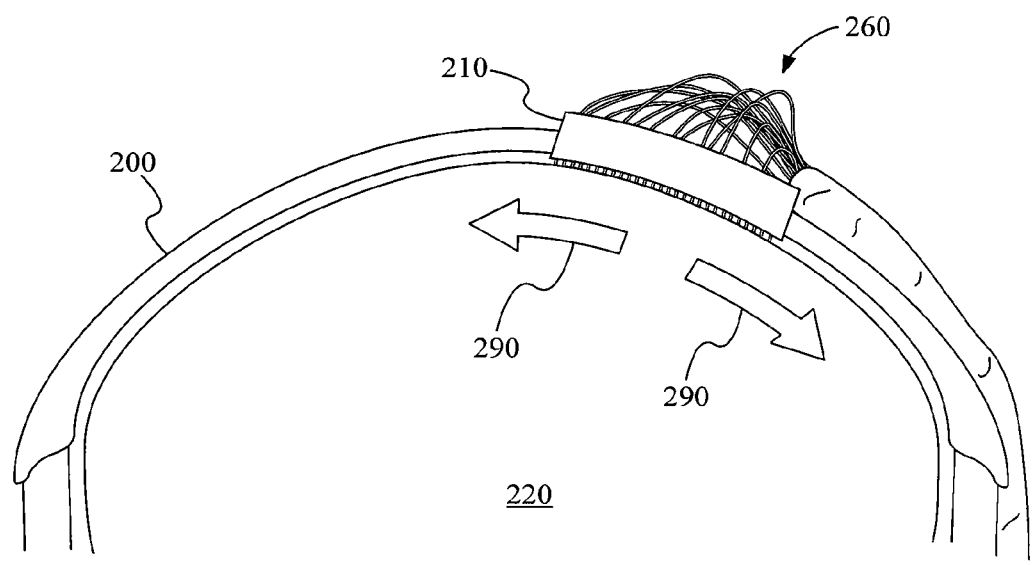
FIG. 2B shows how a brain imaging headset may be repositioned on the scalp according to one embodiment of the invention.

The brain imager may include a number of sensors and/or sources. The sensors and/or sources may be located on an adjustable headset 200 as shown in FIGS. 2A and 2B. The sensors may include optical sources, magnetic sources, photodiodes, magnetic sensors, electrical sensors, etc. The headset 200 may be adjustable such that the sensors and/or sources may be moved to sense different portions of the brain. Moreover, the sensors and/or sources may be localized by the adjustable headset on a specific portion of the scalp above the portion of the motor cortex that is of interest. Moreover, the sensors and/or sources may be configured in a dense pattern within a detector-source array.

Figure 3A:
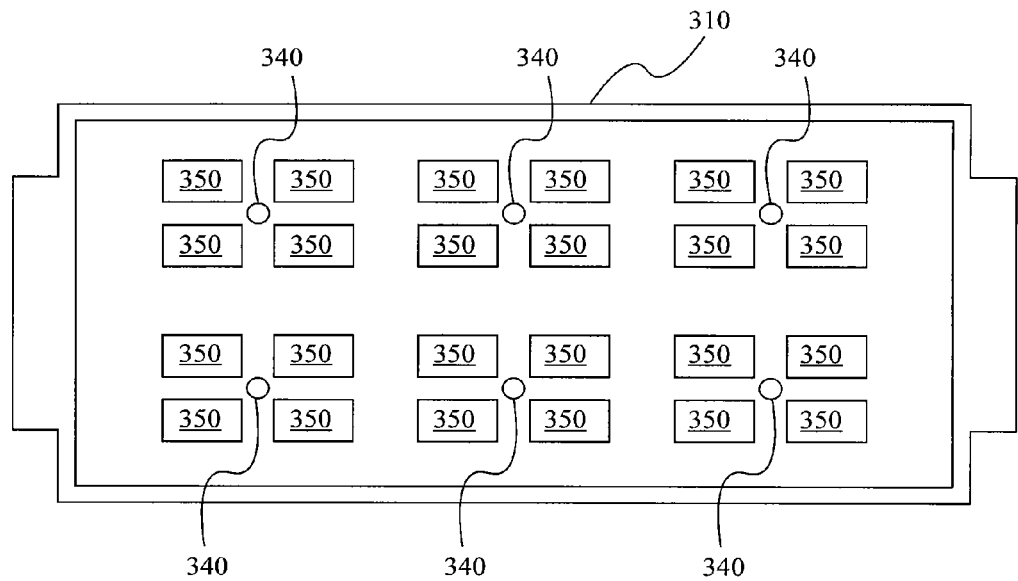
FIGS. 3A, 3B and 3C show configurations of light sources and light detectors for use with a brain imager according to one embodiment of the invention.
Figure 3B:
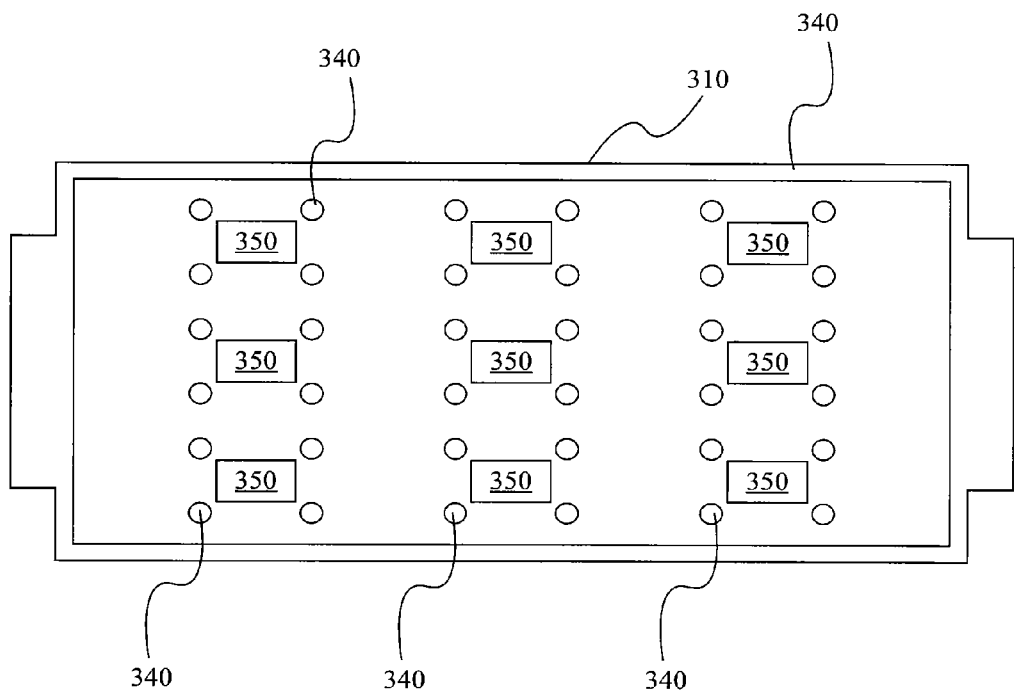
Figure 3C:
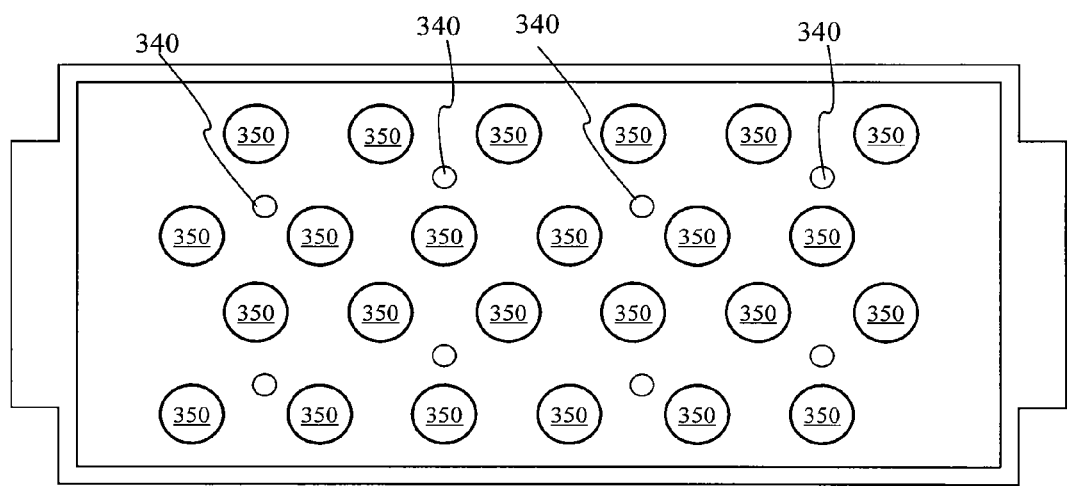

FIGS. 3A, 3B and 3C show various examples of source 340 and sensor 350 configurations according to embodiments of the invention. As shown, the sources 340 and sensors 350 are configured on a sensor-detector array 310. The sensor-detector array 310 may be configured to include one or more sensors 350 and/or sources 340 in localized pattern near an observable portion of the brain. For example, the sensor-detector array may be placed on a user's scalp with the array 310 located over the forearm portion of the motor cortex in order to image the brain activity of the forearm portion of the motor cortex. In another example, the sensor-detector array may be placed on a user's head with the array 310 located over the ankle portion of the motor cortex in order to image the brain activity of the ankle portion of the motor cortex.

A brain imager that focuses on a specific portion of the motor cortex does not image the entire brain or the entire motor cortex. Instead, the brain imager, according to embodiments of the invention, may provide a high density of sources and/or sensors on the sensor-detector array 310. Accordingly, because of the density of sensors over a specific portion of the motor cortex, the brain imager provides a plurality of brain activation signals for a specific motor function. Thus, the brain imager provides greater activation resolution for a specific brain function, for example, specific motor cortex activity.

The brain imager may include a near infrared brain imager, a magnetic resonance brain imager, an electromagnetic brain imager, etc.

A. NIR Brain Imager

Figure 4:
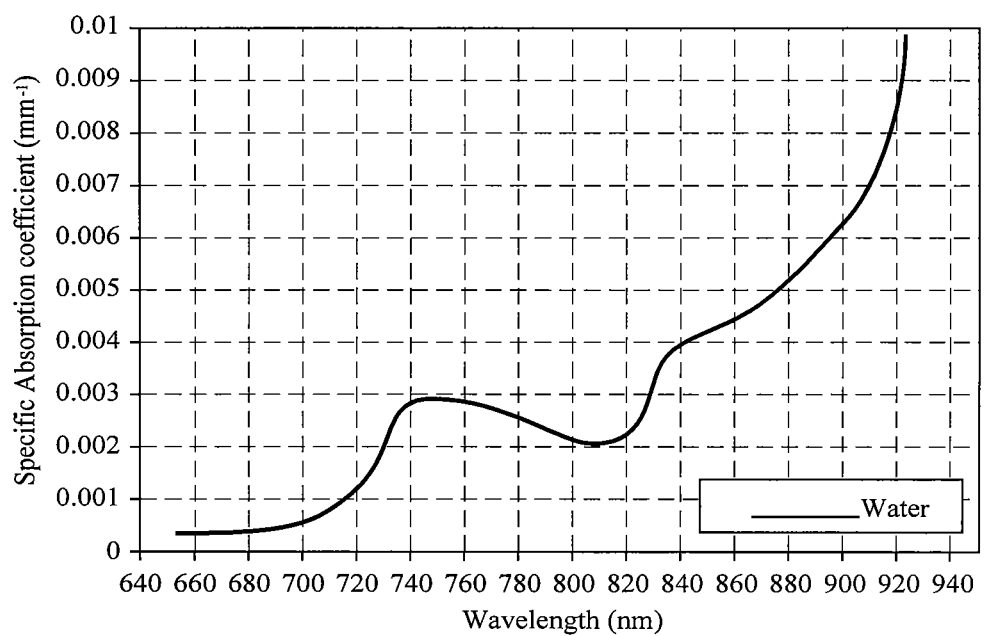
FIG. 4 shows the specific absorption of water versus wavelength.

A near infrared (NIR) brain imager may be used as a specific type of brain imager according to one embodiment of the invention. FIG. 4 shows a graph of the specific absorption coefficient of water versus the wavelength of incident light. As shown, the absorption increases dramatically for light above 820 nm. The absorption of light is low enough in the near infrared (NIR) range that a substantial portion of light in this range is transmitted through water without absorption. Because the human body, including the brain, is comprised mostly of water, NIR light transmits well through the brain.

Figure 5:
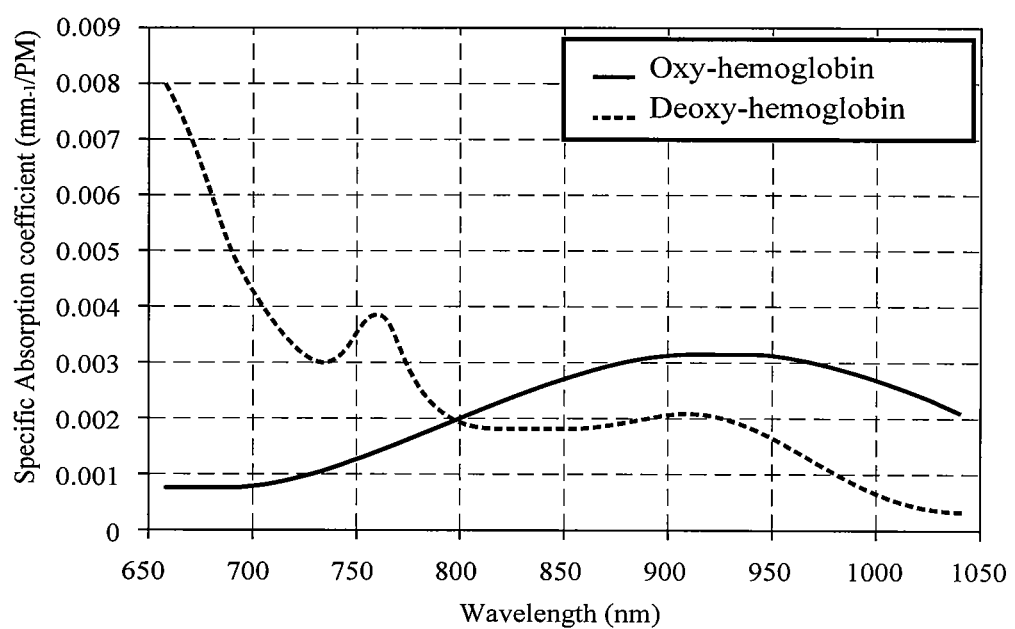
FIG. 5 shows the specific absorption of hemoglobin and oxy-hemoglobin versus wavelength.

FIG. 5 shows the specific absorption of hemoglobin and oxy-hemoglobin versus wavelength in the near infrared. As shown, oxy-hemoglobin and hemoglobin (deoxy-hemoglobin) produce a unique spectral signature within the near infrared spectra. When light passes through tissue, the photons undergo multiple reflections due to scattering objects in their paths, and in the process some of the photons get absorbed by chromophores and/or by other absorbing substances in the tissue, before the light emerges out of the tissue. Accordingly, when light passes through tissue, the tissue imposes its optical signature on the some of the light. By making a comparison between the properties of the light before entering the tissue and after it emerges from the tissue, the optical signature of the tissue can be determined.

Light propagation in tissue is governed by photon scattering and absorption. The overall effect of absorption is a reduction in the light intensity traversing the tissue. The relationship between the absorption of light in a purely absorbing medium and the structure and pigments present in the medium is given by the Beer-Lambert Law. Scattering is the basic physical process by which light interacts with matter. Changes in internal light distribution, polarization, and reflection can be attributed to the scattering processes. Because scattering increases the optical path length of light propagation, photons spend more time in the tissue when no scattering occurs thus changing the absorption characteristics of the medium. Light propagation in a turbid (scattering) medium can be modeled by the modified Beer-Lambert Law (MBLL).

The electromagnetic spectrum has two unique characteristics in the NIR range (700 nm-1000 nm). First, biological tissues weakly absorb NIR light, allowing it to penetrate several centimeters through the tissue and still can be detected. In addition, the dominant chromophores (light absorbing molecules) in the NIR window are oxy-hemoglobin and deoxy-hemoglobin. The principal chromophores in tissue are water (typically 80% in brain tissue), lipids, melanin and hemoglobin. The absorption spectrum of lipids closely follows that of water and melanin though an effective absorber contributes only a constant attenuation. Spectroscopic interrogation of tissue reveals that oxy-hemoglobin (oxy-Hb) and deoxy-hemoglobin (doxy-Hb) are biologically relevant markers, and their neurovascular coupling allows absorption spectra to reliably track neural activity. There are at least three types of NIR imaging: (1) time resolved (TRS), (2) frequency domain (FD), and (3) continuous wave (CW) techniques.

1. Beer-Lambert Law (BLL)

The Beer-Lambert Law is an empirical relationship that maps absorption of light to the properties of the material through which the light is traveling. There are several ways in which the law can be expressed. The transmittance (T) of light through a medium, which is the ratio of the intensity of light that enters a medium ($I_0$) over the intensity of the light that exits the medium ($I_1$) may be expressed as:

$$T = \frac{I_o}{I_l} = e^{-\alpha \cdot l \cdot c} \qquad \text{eq. 1}$$

where $$\alpha = \frac{4\pi k}{\lambda}. \qquad \text{eq. 2}$$

In terms of absorbance (A) of light $$A = \alpha \cdot l \cdot c \qquad \text{eq. 3}$$

$$A = \log \frac{I_o}{I_l}. \qquad \text{eq. 4}$$

where l is the distance that the light travels through the material (the path length), c is the concentration of absorbing species in the material, α is the absorption coefficient or the molar absorptivity of the medium, λ is the wavelength of the light, and k is the extinction coefficient.

Accordingly, the Beer-Lambert Law states that there is an exponential dependence between the transmission of light through a substance and the concentration of the substance, and also between the transmission and the length of material that the light travels through. Thus, if l and α are known, the concentration of a substance can be deduced from the amount of light transmitted by it.

2. Modified Beer-Lambert Law (MBLL)

Figure 6:
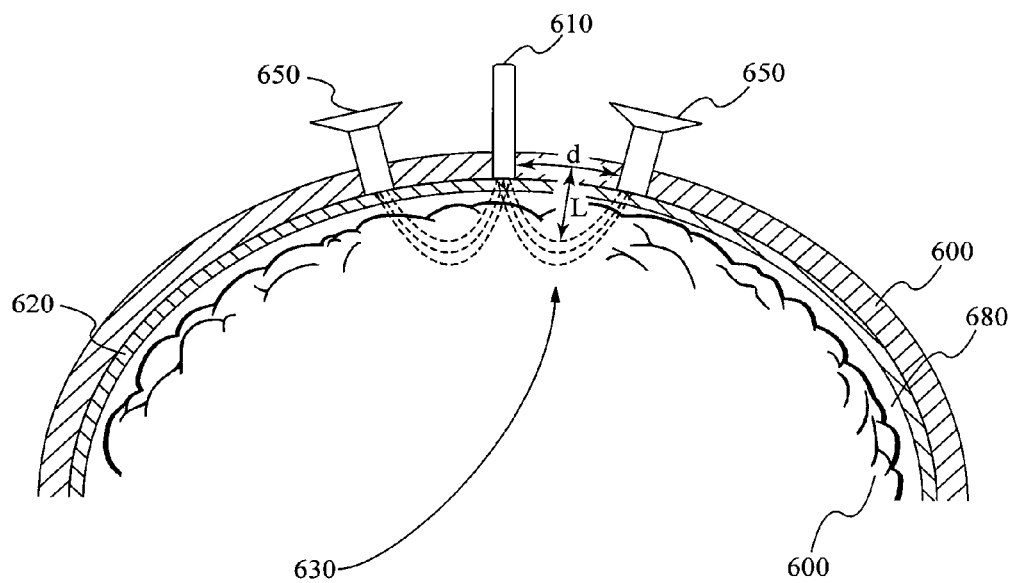
FIG. 6 shows a cut-away of a human skull showing the brain, skull and brain imaging sensors according to one embodiment of the invention.
Figure 7:
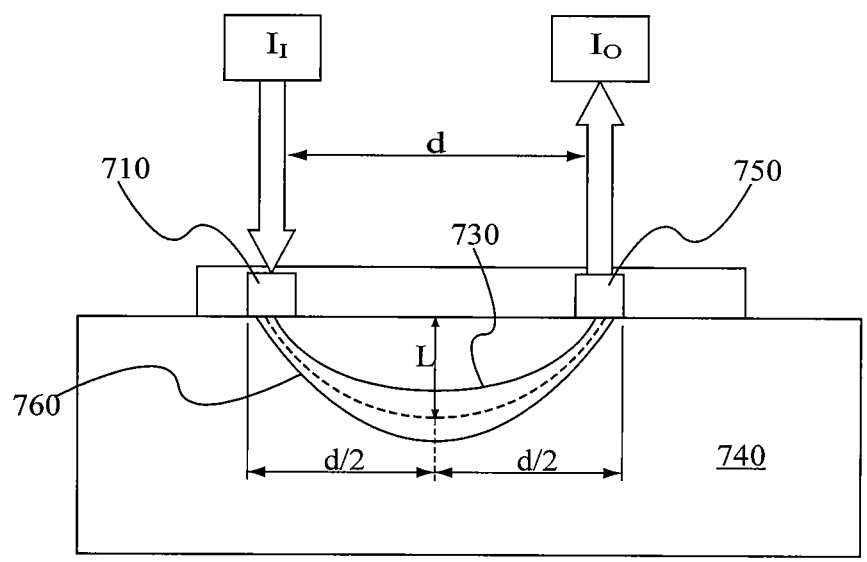
FIG. 7 shows a block diagram of a brain imaging sensor according to one embodiment of the invention.

An example of the geometry of NIR light propagation through the brain is shown in FIG. 6 and depicted schematically in FIG. 7. In FIG. 6, a headband 600 positions a light source 610 on the skull 620 of the user to direct input light at an intensity ($I_1$) to a target tissue area 630 of the brain 640. One light source and two detectors are shown for simplicity and by way of example. An output light intensity ($I_0$) is received by a light detector 650. From the light source 610, light follows a characteristic path 460 through the target tissue 630 back to the light detector 650 on the same approximate plane 670 as the source 610. While the light is severely attenuated by the intermediate tissue 680 (including hair, skin, and bone tissue such as found on a person's head) and by the target tissue 630 due to the scattering and absorption process, it is nonetheless encoded with the spectroscopic signatures of the molecules encountered en route to the light detector 650.

Looking at FIG. 7, fractions of the incident light that are remitted, scattered and absorbed depend on the optical properties of the target tissue 730. The amount of absorption is directly dependent on the chromophore concentration. The optical path 760 taken by remitted photons is a characteristic "crescent shape" whose dimensions, particularly the depth of penetration L, are dictated by the source-detector separation d.

FIG. 7 shows NIR source-detector geometry schematically according to one embodiment of the invention. NIR recordings are basically quantified trend measurements. They do not attempt to predict the absolute oxygen level at any given time, but track neural activity by recording the oxygen level changes with time. By applying MBLL to the source-detector geometry, the following is obtained:

$$A_\lambda = \log_{10}\left(\frac{I_0}{I_l}\right) \approx \varepsilon_\lambda \cdot c \cdot d \cdot DPF + G \qquad \text{eq. 5}$$

Where $A_\lambda$ is the light intensity attenuation for wave length $\lambda$ expressed in terms of optical density (OD). 1OD corresponds to a 10 fold reduction in intensity. $I_1$ and $I_0$ are the input and output light intensities respectively. $\varepsilon_\lambda$ is the absorption factor for wavelength $\lambda$. $\varepsilon_\lambda$ is also called the specific absorption coefficient or the extinction coefficient for wavelength $\lambda$. $\varepsilon_\lambda$ is defined as the numbers of ODs of attenuation produced by the absorber at a concentration of 1 μM (micro moles) and over a physical path of 1 cm, hence the dimensions of OD are $cm^{-1} \mu M^{-1}$. c is the concentration of the chromophore in terms of μM. d is the distance between the source and detector in terms of cm. DPF is the differential pathlength factor, which is a dimensionless constant to account for the photon path lengthening effect of scattering and G is an additive term for fixed scattering losses.

Eq. 5 can be rewritten as:

$$\Delta A_\lambda = \log_{10}\left(\frac{I_0(t)}{I_0(0)}\right) = \Delta c \cdot \varepsilon_\lambda \cdot d \cdot DPF \qquad \text{eq. 6}$$

The two chromophores oxy- and deoxy-hemoglobin can then be taken into account by:

$$\Delta A_\lambda = \log_{10}\left(\frac{I_0(t)}{I_0(0)}\right) = \left(\sum_{i=1}^{2} \Delta c_i \cdot \varepsilon_{\lambda_i}\right) \cdot d \cdot DPF \qquad \text{eq. 7}$$

A similar measurement at another wavelength is needed to solve for the two Δc, turning eq. 7 into a matrix-vector:

$$\underbrace{\begin{bmatrix} \Delta A_{\lambda 1} \\ \Delta A_{\lambda 2} \end{bmatrix}}_{A} = \frac{1}{d} \underbrace{\begin{bmatrix} \dfrac{\varepsilon_{\lambda 1 \cdot oxyHb}}{DPF_{\lambda 1}} & \dfrac{\varepsilon_{\lambda 1 \cdot doxyHb}}{DPF_{\lambda 1}} \\ \dfrac{\varepsilon_{\lambda 2 \cdot oxyHb}}{DPF_{\lambda 2}} & \dfrac{\varepsilon_{\lambda 2 \cdot doxyHb}}{DPF_{\lambda 2}} \end{bmatrix}}_{\varepsilon} \underbrace{\begin{bmatrix} \Delta c_{oxyHb} \\ \Delta c_{doxyHb} \end{bmatrix}}_{C} \qquad \text{eq. 8}$$

Careful selection of the wavelengths will result in a nonsingular $\varepsilon$ allowing solution by direct matrix inversion. The final two measures of oxygenation (oxy), and blood volume (BV), are extracted from the $\Delta c_i$ as:

$$\text{oxy} = \Delta C_{oxyHb} - \Delta C_{doxyHb} \qquad \text{eq. 9}$$

$$\text{BV} = \Delta C_{oxyHb} + \Delta C_{doxyHb} \qquad \text{eq. 10}$$

Dimensions of both oxy and BV are in μM. An accurate value of DPF accounting for its dependence on wavelength is give by:

$$DPF_\lambda = \frac{1}{2}\left(\frac{3\mu'_{s\lambda}}{\mu_{a\lambda}}\right)^{\frac{1}{2}}\left[1 - \frac{1}{1 + d(3\mu'_{s\lambda}\mu_{a\lambda})^{\frac{1}{2}}}\right]. \qquad \text{eq. 11}$$

where $\mu'_{s\lambda}$ is the reduced scattering coefficient of blood at wavelength $\lambda$ and $\mu_{a\lambda}$ is the absorption coefficient of blood at wavelength $\lambda$.

The depth of light penetration (L) in FIG. 7 plays a role in the information content of the extracted signal. Optical neural-imaging involves light propagation through layers of heterogeneous tissue with cerebrospinal fluid (CSF) influencing the depth of light penetration.

B. Exemplary Brain Imager

With the analytical framework discussed above in regard to the BLL and MBLL in mind, a NIR brain imager may provide relative oxy and deoxy-hemoglobin measurements from the intensity of light transmitted into a portion of the brain ($I_1$) and the intensity of light received from the portion of the brain ($I_0$). One embodiment of the invention uses coherent light sources, such as LEDs or lasers, with peak frequencies centered at 735 nm and 850 nm. The brain imager may also include one or more light detectors, such as photodiodes, that detect light transmitted into the brain by the light source(s). For example, a single light source may be surrounded by an array of six photodiodes at 735 nm and an array of six diodes at 850 nm within a single source/detector package. Other examples may include a light source with three photodiodes at 735 nm and 850 nm. In yet another example, a detector at 735 nm and 850 nm may be surrounded by four light sources. Such configurations may generate enough power to provide a sufficient signal back from the brain. Another embodiment uses LEDs with a single filament at each wavelength and a smaller distance between source and receiver to compensate for signal loss. The two wavelengths being used cannot be adjusted inasmuch as these wavelengths correspond with the spectrally significant portions of the signal received back from the brain. Various source/detector configurations may be used. In some embodiments, multiple light sources may be included with a single detector and vice versa.

FIGS. 2A and 2B show examples of an optical brain imager 200 according to one embodiment of the invention. As shown, a headset is shown with a number of fiber optic cables 240 that transmit light to and from the surface of the scalp. It is to be understood that any other suitable device could be utilized to incorporate the brain imager such as a headband, a cap, a support fixture, etc. The headset 200 of FIG. 2B positions the array 210 above the head 220 of the user 230 a given distance so that the fiber optics 240 extend downwardly from the array 210 through the hair (not shown) to touch the scalp. The headset 200 can be placed as close to the scalp as possible. The distance that the fiber optics 240 extend below is dependent on how close the headset 200 is to the scalp. One end of the fiber optics 240 is positioned as close to the scalp as possible and the other end can be coupled with a light source or light detector to transmit or receive light.

C. Sensor-Detector Array

The array 310, as shown in FIG. 3A, is a 6×24 array, that is six light sources 340 are surrounded by four light detectors 350. As shown in FIGS. 2A and 2B, in one embodiment of the invention, thin optical fibers shine light from light sources between hair (not shown) to the scalp, and fiber optics can detect neural-imaging signals and return the light from the surface of the scalp to a light detector. The fiber optics are coupled with the light sources and the detectors. The light sources and detectors are located in a separate unit that is shoulder or back-mounted with no electrical wires being run to the headset. The light is brought up to the headset and back down from the headset via optical fibers. Accordingly, fiber optics may be considered part of the light sources and/or part of the light detectors.

As shown inn FIG. 3A, the spacing of the sensors may be 1.41 inches from center to center in a uniform pattern both across and along the length of the device. This spacing (square-root of 2) places the light sources 1.00 inch from all surrounding light detectors (center to center) 350. Various other dimensions may also be used. FIG. 3B shows light detectors 350 surrounded by a plurality of light sources 340 in another geometric pattern. The sensors and/or light sources may include a fiber optic. FIG. 3C shows another array with each light detector 350 is surrounded by three light sources 340. Various other sensor and light source configurations may be used without deviating from the spirit of the invention. Light detectors 350 and light sources 340 may be about 0.5, 1.0, 1.5, 2.0, 2.5, 3.0, 3.5, etc. centimeters apart. Moreover, the sensors 350 and light sources 340 may be configured in any pattern and may be positioned away from the array but coupled thereto with fiber optics.

The array may present light sources and/or detectors at portions of the scalp corresponding to the pre-motor cortex and/or the motor cortex.

In one embodiment of the invention, the sensor-detector array may include a plurality of fiber optics. Each fiber optic may be associated with a light source or a photodiode at either a first or second wavelength. The fiber optics may be arranged in any of a number of patterns. The density of the fiber optics may also vary. The sensor-detector array provides light and receives light from a specific portion of the scalp.

Figure 8:
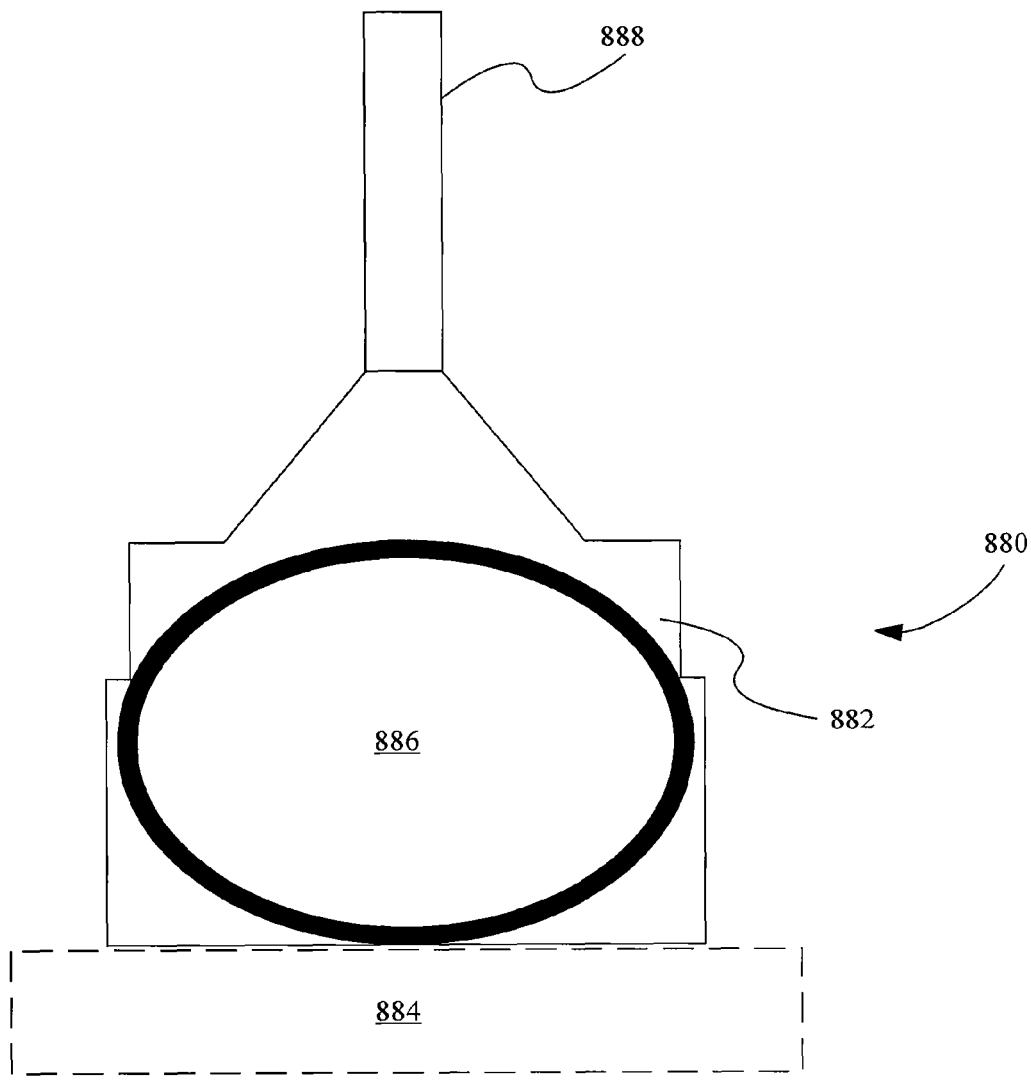
FIG. 8 shows a fiber optic connector according to one embodiment of the invention.

FIG. 8 shows a fiber optic connection apparatus 880 according to one embodiment of the invention. The apparatus includes a housing 882 for holding an LED 884, a ball lens 886, and a fiber 888 for carrying light emitted from the LED 884 through the ball lens 886 to the end of the fiber optic.

Figure 9:
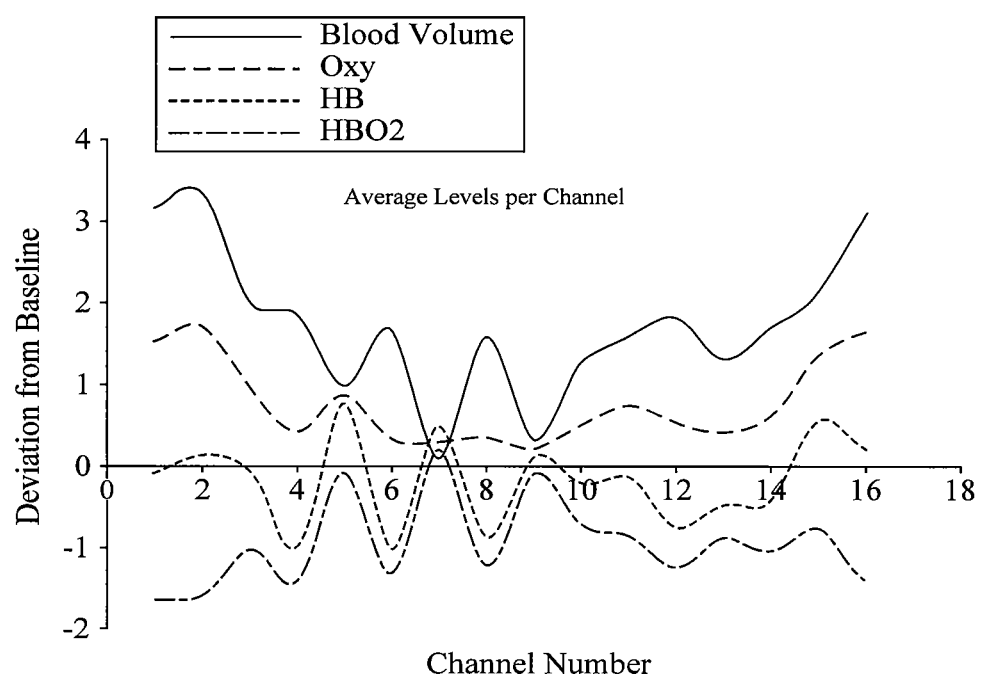
FIG. 9 shows a graph of the averaged levels per channel obtained using one embodiment of the brain imager of the present disclosure.

FIG. 9 shows a graph of the relative levels of blood volume, oxygen, hemoglobin, and oxy-hemoglobin from a system employing various embodiments of the invention. Ten photodiodes and four light sources were used to create a 16-channel detector. The optical brain imager was used on six human subjects. These subjects were asked to perform some movements while the photodiode outputs were being collected. During a seated leg lift, the general tendency was for oxygenated blood volume to decrease and deoxygenated blood volume to increase in areas of the brain that were activated by the movement. The odd numbered channels represented the front row of detectors and even numbered channels represented the back row of detectors.

In another embodiment of the invention, the array includes a 20×80 array. Such an array may obtain more data points with a higher sensor density or a larger monitoring area. Other array configurations may be used, for example, arrays with 10, 20, 30, 40, 50, 60, 70, or 80 light detectors and arrays with 10, 20, 30, 40, 50, 60, 70, or 80 light sources may be used. Any other combination of light sources and/or light detectors may be used.

In another embodiment of the invention, a plurality of sensor arrays are provided. Each of the sensor arrays may be used to sense brain activity at a different specific portion of the brain. For example, a headset may be coupled with two sensor arrays. One sensor array may be positioned over the wrist control portion of the motor cortex and the other sensor array may be positioned over the elbow control portion of the motor cortex. Thus, activation of brain activity in either the wrist and/or the elbow motor cortices will provide signals to a controller that may be used to control the wrist and/or elbow. Any number and/or combinations of motor cortex arrays may be imaged. In yet another embodiment of the invention, a headset may include a plurality of arrays, where each array includes a small number of densely packed light sensors and/or light detectors. For example, a head set may include four arrays with each array containing six light detectors and six light sources.

II. Neuro-Fuzzy Inference Engine

A neuro-fuzzy inference engine is also provided for mapping brain activity data into limbic control signals according to one embodiment of the invention. Mapping brain activity to limbic control can be seen as an inverse nonlinear problem with some level of uncertainty due to the finite resolution of optical brain imager. A mix of neural network and fuzzy logic may be incorporated in the inference engine. While various inference engines, if/then engines, neural networks or the like may be used to map brain activity data to limbic control, a neuro-fuzzy inference engine is provided as one example.

Figure 10:
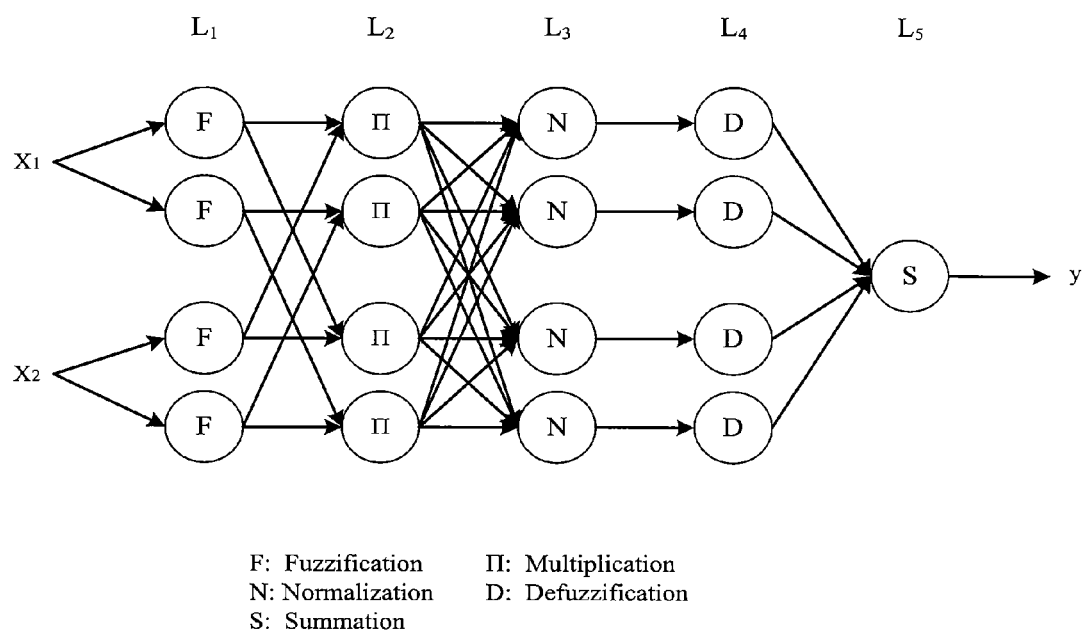
FIG. 10 shows a block diagram of a multilayered fuzzy neural network according to one embodiment of the invention.

A neuro-fuzzy inference engine may have five layers, in one embodiment, and can be used for any number of multi-inputs and multi-outputs (MIMO). The neuro-fuzzy inference engine employs the gradient descent method and the least square estimation (LSE) algorithms to train the network. FIG. 10 shows the architecture of the inference engine.

Layer 1 ($L_1$) is a fuzzification layer. Each node generates a membership degree of a linguistic value. The $k^{th}$ node in this layer performs the following operation:

$$O_l^1 = O_{ij}^1(x_i) = \frac{1}{1 + \left(\frac{x_i - a_{ij}}{b_{ij}}\right)^2} \quad \text{eq. 12}$$

where j is the number of membership functions, i is the number of input variables, $l=(i-1)\cdot n_{+,i}+j$ and $x_i$ is the $i^{th}$ input variable. The antecedent parameters $\{a_{ij}, b_{ij}\}$ are a set of parameters associated with the $j^{th}$ membership function of the $i^{th}$ input variable and used to adjust the shape of the membership function during training.

Layer 2 ($L_2$) is a multiplication layer. At the multiplication layer, each node calculates the firing strength of each rule by using multiplication operation.

$$O_k^2 = \prod_i O_{ij}^1(x_i)(1 \le k \le 4),\qquad \text{eq. 13}$$

where k is an integer between 1 and the number of nodes in the second layer and $O_k^2$ is the output of the $k^{th}$ node in the second layer.

Layer 3 ($L_3$) is the normalization layer. The number of nodes in this layer may be the same as the first layer. The output of layer 3 is determined according to:

$$O_k^3 = \frac{O_k^3}{\sum_k O_k^2}(1 \le k \le 4).\qquad \text{eq. 14}$$

Layer 4 ($L_4$) is the defuzzification layer. The number of nodes in this layer may be equal to the number of nodes in layer 1 times the number of output variables. The defuzzified value for the $k^{th}$ rule is $$y_k = \begin{cases} c_k - d_k\sqrt{\frac{1}{O_k^3} - 1} & \text{if } k = \text{odd} \\ c_k + d_k\sqrt{\frac{1}{O_k^3} - 1} & \text{if } k = \text{even} \end{cases}(1 \le k \le 4)\qquad \text{eq. 15}$$

where $\{c_k, d_k\}$ are consequent parameters and are used to adjust the shape of the membership function of the consequent part. Then, the output of layer 4 becomes:

$$O_k^4 = O_k^3 \cdot y_k = \begin{cases} O_k^3 \cdot \left(c_k - d_k\sqrt{\frac{1}{O_k^3} - 1}\right) & \text{if } k = \text{odd} \\ O_k^3 \cdot \left(c_k + d_k\sqrt{\frac{1}{O_k^3} - 1}\right) & \text{if } k = \text{even} \end{cases}\qquad \text{eq. 16}$$

$(1 \le k \le 4)$.

Layer 5 is the summation layer. Here, the number of nodes is equal to the number of outputs. There is only one connection between each node in layer 3 and a node in the output layer:

$$O_1^5 = \sum_k O_k^4 (1 \le k \le 4),\qquad \text{eq. 17}$$

In the training process, the engine tries to find the minimizing error function between target value and the network output. For a given training data set with P entries, the error function is defined as:

$$E = \sum_{p=1}^P E_p = \frac{1}{2}\sum_{p=1}^P (T_p - O_{1,p}^5)^2, (1 \le p \le P)\qquad \text{eq. 18}$$

where $O_1^5$ is the $p^{th}$ output of the network and $T_p$ is the $p^{th}$ desired target. The premise parameters $\{a_{ij}, b_{ij}\}$ are updated according to a gradient descent and the consequent parameters $\{c_k, d_k\}$ are updated using a LMS algorithm.

The neuro-fuzzy inference engine provides a combination of a fuzzy inference engine and an adaptive neural network. The neuro-fuzzy inference engine uses fuzzy reasoning for both fuzzification and defuzzification, that is, the membership functions may be monotonic nonlinear functions.

As described above, the neuro-fuzzy inference engine can be applied to multi-input and multi-output (MIMO) systems. For example, a system with 20 inputs corresponding to brain activation within a portion of the brain may provide two outputs corresponding to limbic control related to a flexor muscle and a extensor muscle. Various other embodiments may include any number of inputs of brain activity and any number of outputs corresponding to limbic control.

The neuro-fuzzy inference engine may use associated hybrid learning algorithms to tune the parameters of membership functions such as feedforward processes; least square estimation; backward process; gradient descent method, etc. The engine may also use an optimal learning rate that is updated after each learning process. The neuro-fuzzy inference engine may also use the least number of coefficients to learn and has a fast convergence rate.

The inference engine may integrate features of a fuzzy system (fuzzy reasoning) and neural networks (learning). Neuro-fuzzy inference technique may provide a means for fuzzy modeling to learn information about a data set, which will compute and generate the membership function parameters, so that the associated fuzzy inference system can track the given input and output pattern. The inference engine's learning method works similarly to that of neural networks. This network can be used to find out system parameters and unknown factors through the training process, which means it achieves the goal of system identification.

While this represents one mathematical approach in a five level process, it is to be understood that other mathematical variations and/or designs could be utilized in the inference engine. In addition to this neuro-fuzzy inference engine, signal processing may occur. For example, the data may be mean zeroed, time domain shifted, or filtered using a band-pass filter of any order, or may extract maximums and minimums, construct time domain file, remove leading and trailing data points, apply averages, resample data, apply noise reduction algorithms, etc. As a specific example, the following eight-step signal processing may be performed on the data prior to giving it to the neuro-fuzzy system. The following highlights those eight steps: 1) obtain ASCII coded frequency sweep data files, 2) make data sets mean zeroed 3) apply $5^{th}$ order band-pass filter, 4) overlap data files on a time domain, 5) extract the maximum value from each piece of band-passed and filtered data, and construct a one time domain data file, 6) remove the first 900 points and last 3000 data points, 7) apply a running average filter (with summing every 50 data points), and 8) re-sample every $6^{th}$ order data.

III. Training System

Neural network training systems and methods are provided according to one embodiment of the invention. In order to train a neural network, inputs and corresponding outputs may be provided so that the weighting of each input can be established based on the known outputs. In the case of training a brain imager, the data collected by the brain imager acts as the input signals while electromyography (EMG) data, for example, provides data for known outputs. EMG provides physiological responses of muscles at rest and during contraction. The training system correlates EMG data with the brain activity data provided by the brain imager. This correlation may occur using a neural network and/or a neuro-fuzzy network.

EMG units may be placed on the muscle group(s) of interest. An EMG unit (electromyograph) may detect the electrical potential generated by muscle cells when in contraction or at rest. An EMG unit may measure the magnitude and/or frequency of the electric potential. A surface or needle electrode may be used. Various other EMG units may be used without deviating from the spirit of the invention.

Training a system for elbow and wrist actuation, for example, may use four EMG units placed at the four major muscle groups that control forward and reverse motion of the wrist joint. Activation of flexor muscles indicates a forward actuation of the corresponding joint and activation of extensor muscles indicates a reverse actuation of the corresponding joint. Accordingly, the EMG units are placed on the flexor and extensor muscles as needed.

During training, a brain imager is placed over the portion of a user's motor cortex that controls the wrist. EMG units are placed on the wrist extensor and flexor muscles. The user is then asked to move the wrist in a variety of ways. Brain activation data and EMG data are captured during the wrist motion. Data sets that correspond brain activation to EMG data may then be provided to a control system, such as a neural network. The data sets may be used by the neural network to adjust the neural network constants in such a way that the neural network provides the outputs that correspond to the EMG data in response to inputs that correspond to brain activation data.

By recording EMG and brain imaging data at the same frequency, matching sets of inputs and outputs are provided to the fuzzy neural training system. After training has been completed, the EMG units can be removed from the system and an artificial limb may be controlled using the algorithms developed by the neural network.

The neural network may also include feedforward and feedback controls. For example, brain activation signals are provided as feedforward signals and the EMG signals are feedback signals. The combination of feedforward and feedback signals may be used to train the neural network.

IV. Brain Imager and Prosthesis Control System

Figure 11:
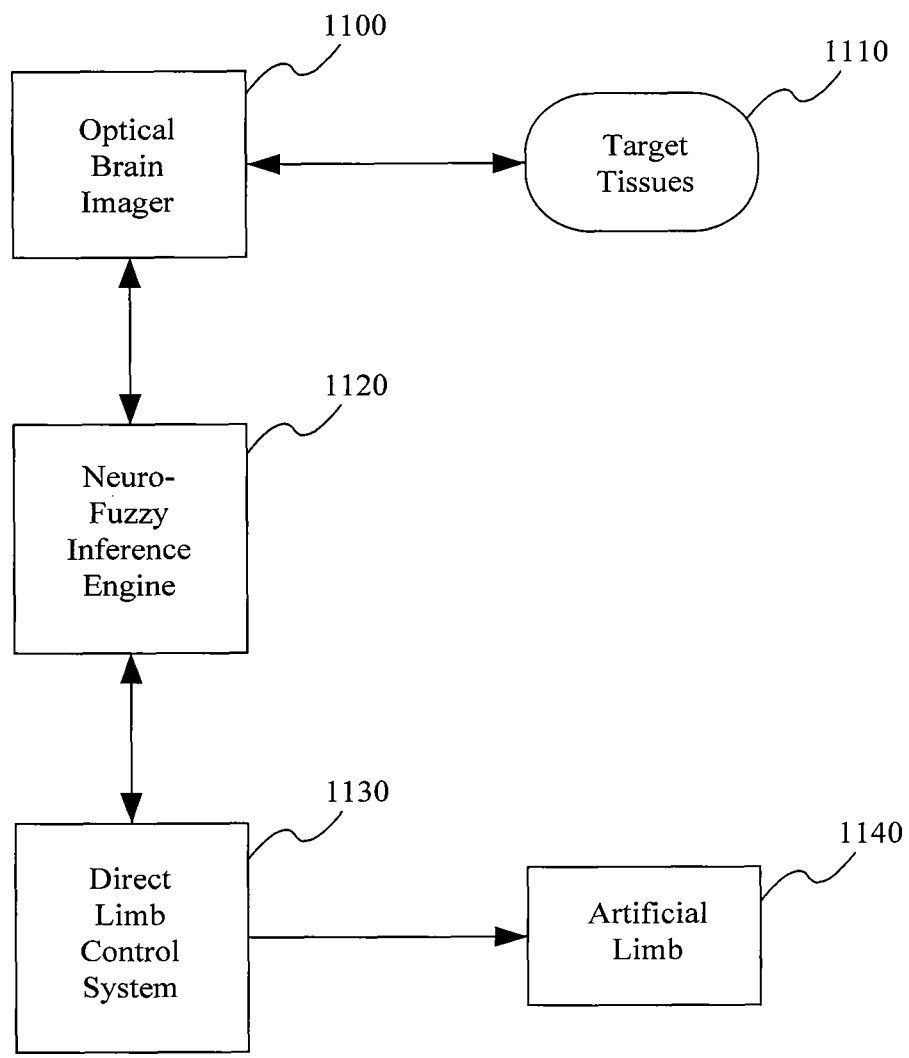
FIG. 11 shows a block diagram of a prosthesis control system using a brain imager according to one embodiment of the invention.

A brain imaging and prosthesis control system is also provided according to one embodiment of the invention. FIG. 11 shows a high-level block diagram of a prosthesis control system according to one embodiment of the invention. An optical brain imager 1100 images target tissues 1110. The target tissues may include portions of the motor cortex. The optical brain imager 1100 may provide signals from the brain to a neuro-fuzzy inference engine 1120 that maps brain activation data to limbic control signals. The neuro-fuzzy inference engine 1120 communicates limbic control signals to a direct limb control system 1130 that controls an artificial limb.

Figure 12:
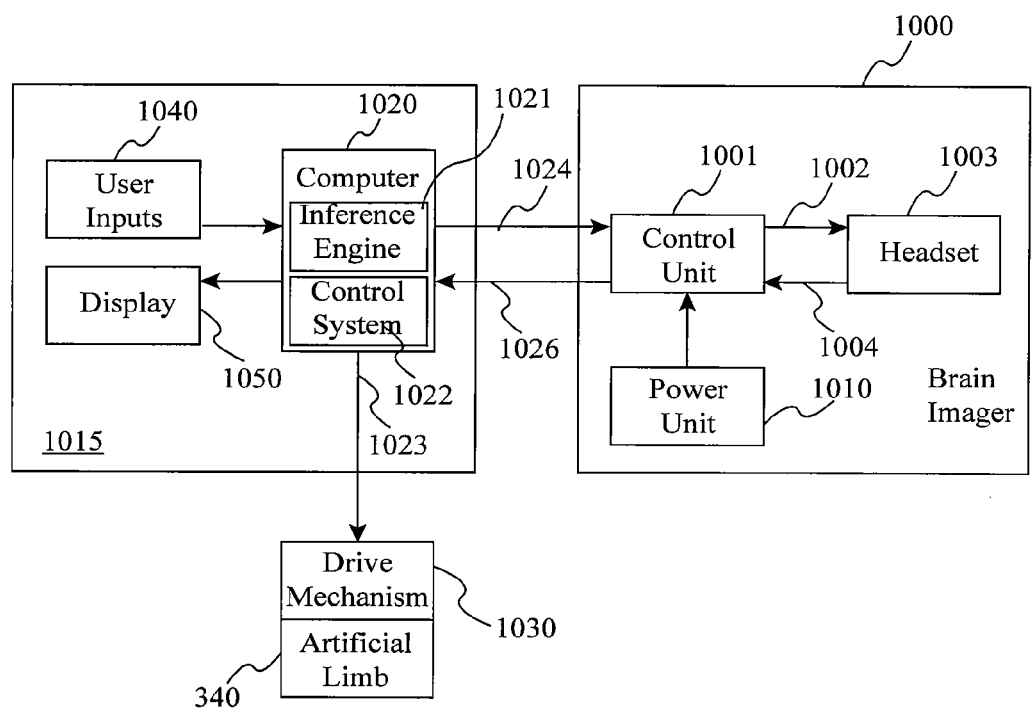
FIG. 12 shows a block diagram of a system for controlling a prosthesis using a brain imager according to one embodiment of the invention.

FIG. 12 shows a block diagram of a brain imaging and prosthesis control system according to another embodiment of the invention. A brain imager 1000 includes a headset 1003 carrying the fiber optics, the LEDs, and/or the photodiodes. The headset 1003 is connected to a control unit 1001 which provides control signals 1002 to the headset, photodiodes, and/or LEDs and receives data signals back 1004. The LEDs may be substituted with other light sources, such as, for example, lasers. Moreover, the photodiodes may be substituted with other light detectors.

Light source power may be controlled by adjusting the supply current. According to one embodiment of the invention, four LEDs are used that are sequentially turned on and off. In such a configuration, only one LED is on at a given time. The pulse duration of the LEDs may be less than 0.086 seconds. Other pulse durations may be used. The control unit may comprise a compact unit that may be worn on the shoulder or upper back. The power unit 1010 may use any suitable power source such as solar power, rechargeable battery power, battery power, etc.

The brain imager 1000 is coupled with a controller 1015 that may include a microcontroller 1020 which may incorporate both the inference engine 1021 and the direct limb control system 1023. The microcontroller 1020 sends command signals 1023 to the drive mechanism 1030 of the artificial limb 340 of the present invention to provide the signals that may actuate the artificial limb 340. Such drive mechanisms 1030 for the artificial limbs are commercially available. Various other robotic and/or prosthetics may be used in place of an artificial limb.

The user of the optical brain imager 1000 of the present invention may act as a portion of the feedback control loop for the artificial limb according to one embodiment of the invention. The user can see the movement of the limb and adjust limbic control accordingly. The feedback the user experiences may only provide visual confirmation of the location of the arm and any force or movement induced on the artificial limb when it connects to the patient's body. As a result the brain changes the degree of effort put into moving the limb to stop or accelerate motion, which is in turn detected by the optical brain imager 300 and leads to changes in the control signals sent to the limb.

In FIG. 12, the computer 1020 provides control signal 1024 to the brain imager control unit 1000 and receives data signals 1026 from it. The difference between the data streams 1024, 1026, 1002, and 1004 is that the data leaving the control unit has been processed (1002 and 1026). In the case of 1024 to 1002, the data has been modified from computer signals into a power. In the case of 1004 to 1026, the data has been changed from raw current measurements to computer-friendly information. The control unit performs the necessary amplifications and channel switching to convert computer commands to LED control and diode responses back to computer data. The computer 1020 is also connected to receive user inputs 1040 and to display results 1050. The computer may be a microcomputer, processor, microprocessor, etc. The user inputs and display results are both accomplished within an executable program that allows textual control of power levels, displays the incoming data in a graphical format, and records incoming data to a file. However, in other embodiments, these functions are embedded in a small microcontroller, e.g., a PC104 platform.

Figure 13:
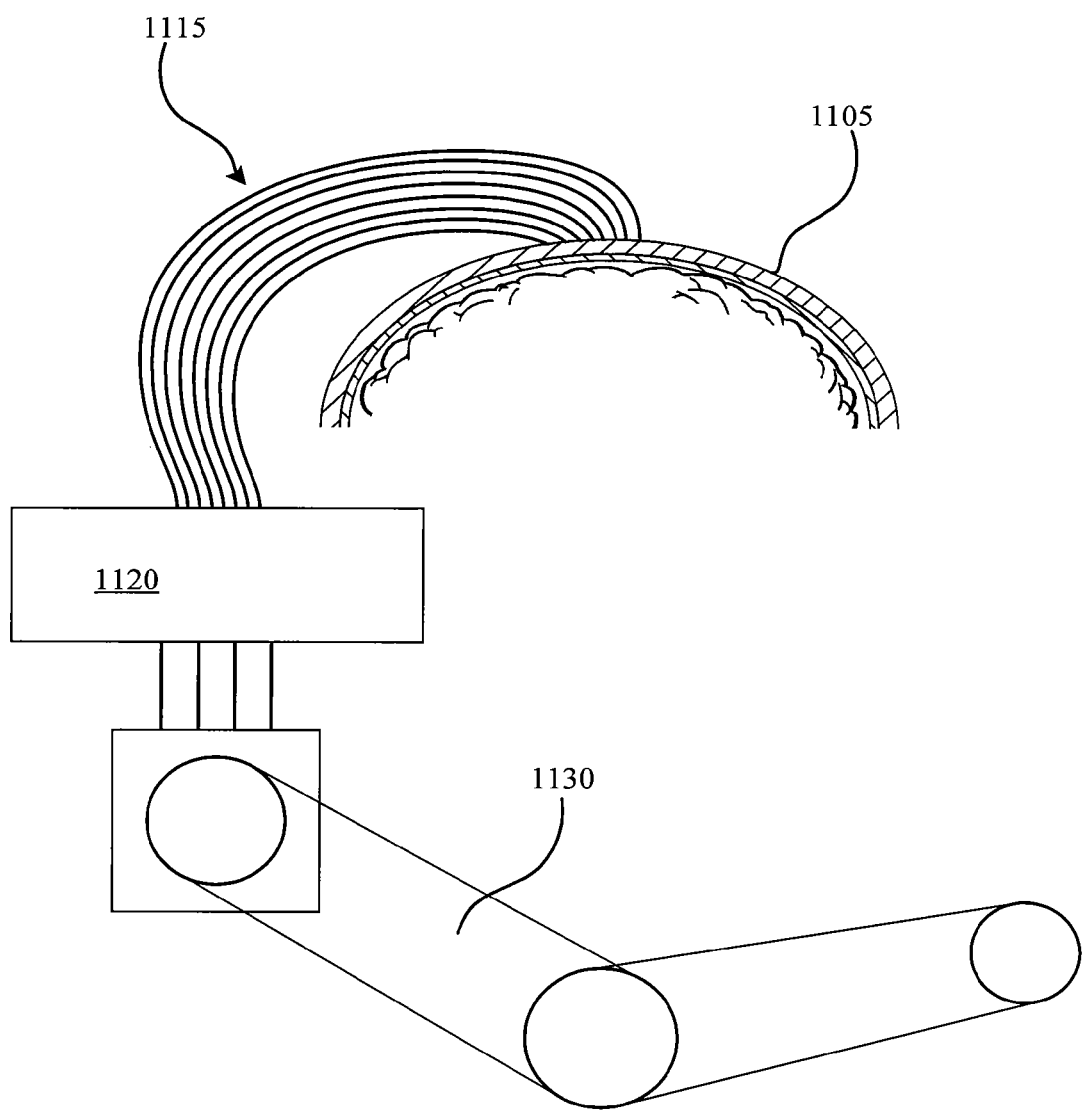
FIG. 13 shows a high level view of a prosthetic control system using a brain imager according to one embodiment of the invention.

FIG. 13 shows another prosthesis control system using a brain imager according to one embodiment of the invention. Fiber optics 1115 channel light to and from the surface of a user's scalp using a headset 1105. Detectors record brain activity within the motor cortex. These signals are provided to a neural-network 1120 which provides control signals for a prosthesis 1130.

Tele-operated devices controlled by neural commands could be used to provide precise human manipulation in remote or hazardous environments, and neural controlled prosthetic limb could return function to a paralyzed patient by routing neural commands to actuators. Studies have shown that patients who have already had a limb removed still exhibit activation of the brain in the areas that correspond with the muscle groups of the missing limb. This phenomenon is referred to as "phantom limb" and allows patients who no longer have muscle or nerve ending in the vicinity of the missing limb to activate the optical brain imager since their brain still attempts to send the signals. Thus, the output of the neuro-fuzzy inference engine and the brain imager 300 provide limbic control signals. One, two, three, four, five, six, seven, eight, nine, ten, eleven, or twelve signals, for example, may be provided for a single joint or motion.

Figure 14:
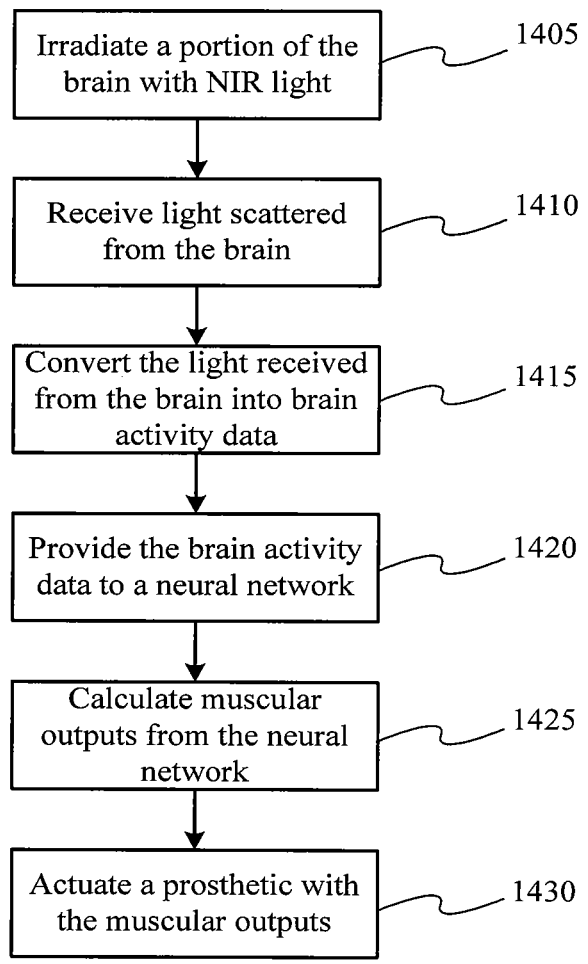
FIG. 14 shows a flowchart showing a method for using a brain imager for determining brain activity related to a portion of the motor cortex that is translated into actuation of a prosthesis according to one embodiment of the invention.

A flowchart outlining a method for providing prosthetic limbic control from a brain imager is shown in FIG. 14 according to another embodiment of the invention. A portion of the brain is irradiated with NIR light at block 1405. The portion of the brain irradiated with NIR light is localized on a portion of the motor cortex of interest. Light from the brain is detected at block 1410. The received light is converted into brain activation data at block 1415. Photodiodes may be used to convert the optical signals to brain activation data. As described above, by irradiating the motor cortex with light of two different wavelengths, one may determine the relative levels of oxy and deoxy-hemoglobin that correspond to brain activity. The brain activity data is then provided to a neural network, for example, a fuzzy neural network at block 1420. Muscular outputs are then provided that correspond to the received brain activity at block 1425. These muscular outputs may then be used to operate or control a prosthesis.

V. Hair Penetrating Fiber Optic

Figure 15A:
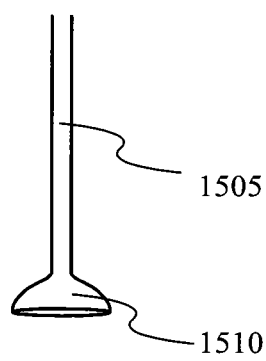
FIGS. 15A and 15B show two exemplary ends of a fiber optic according to one embodiment of the invention.
Figure 15B:
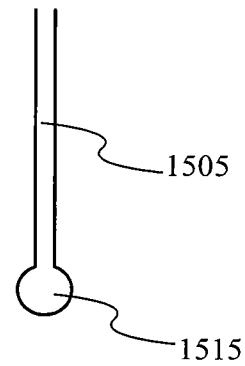

FIGS. 15A and 15B show fiber optics that provide light to and detect light from the scalp through hair according to one embodiment of the invention. In FIG. 15A, the fiber optics 1505 has a distal tip that includes a bulb 1510. The bulb may include a flange and/or cone shaped material. In FIG. 15B, the distal end of the fiber optic includes a ball 1515. Both the ball 1515 and the bulb 1510 may be used to channel light to and/or from the surface of a scalp through hair. The ball 1515 and bulb 1510 may be comprised of the same material as the fiber optic. The ball 1515 and bulb 1510 may be fused with the fiber optic. Such optical fibers are capable of providing light to the surface of the scalp or receiving light from the surface of the scalp through hairs.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method for controlling a prosthesis, the method comprising:
   receiving a brain-activity signal from a brain imager, wherein the brain-activity signal corresponds to brain activity within a portion of the motor cortex;
   mapping the brain-activity signal to a limbic-control signal using a neural network that is trained to map the brain-activity signal to the limbic-control signal; and
   coupling the limbic-control signal with the prosthesis, wherein the prosthesis is configured to respond to the limbic-control signal.

2. The method according to claim 1, further comprising:
   illuminating light on a portion of the brain using a light source; receiving a light signal at the scalp using a photodiode, wherein the detected light travels from the light source through a sub-portion of the brain and is detected at the photodiode; and outputting a brain-activity signal.

3. The method according to claim 2, wherein the light source illuminates a portion of the brain with near infrared light.

4. The method according to claim 1, wherein the neural network comprises a fuzzy neural network.

5. The method according to claim 2, wherein the light source comprises at least one or more LEDs and one or more lasers.

6. The method according to claim 2, wherein the illuminating comprises channeling light from the light source to the scalp.

7. A prosthesis control system, the prosthesis control system comprising:
an optical brain imager configured to:
irradiate a first portion of the brain with one or more light sources;
detect, using one or more photodiodes, a portion of the light transmitted into the first portion of the brain, wherein the detected light travels at least from the one or more light sources through a plurality of sub-portions of the brain and is detected at the plurality of photodiodes;
determine the relative concentration of oxy-hemoglobin within the first portion of the brain from the plurality of photodiodes inputs;
determine the relative concentration of hemoglobin within the first portion of the brain from the plurality of photodiodes inputs; and
determine the brain activity at a plurality of sub-portions of the first portion of the brain from the relative concentrations of oxy-hemoglobin and hemoglobin;
a neural network that is trained to map brain activity to limbic-control signals; and
a controller configured to receive the limbic control signals from the neural network and configured to operate the prosthesis in response to the limbic control signals.

8. The prosthesis control system according to claim 7, wherein the one or more light sources comprise at least one or more LEDs and one or more lasers.

9. The prosthesis control system according to claim 7, further comprising a plurality of fiber optics, wherein the fiber optics are configured to channel the light from the light sources to the surface of the scalp.

10. The prosthesis control system according to claim 7 further comprising a plurality of fiber optics, wherein the fiber optics are configured to channel light from the surface of the scalp to the photodiodes.

11. The prosthesis control system according to claim 7, wherein the plurality of light sources generates near infrared light and the photodiodes receive near infrared light.

12. The prosthesis control system according to claim 7, wherein the plurality of light sources generates light between about 700 nm and about 775 nm.

13. The prosthesis control system according to claim 7, wherein the plurality of light sources generates light between about 800 nm and about 900 nm.

14. The prosthesis control system according to claim 7 further comprising a headset coupled with at least one of an end of the fiber optics and the photodiodes.

15. The prosthesis control system according to claim 14, wherein the headset is configured to adjust the positioning of the fiber optics and the photodiodes over different portions of the brain.

16. The prosthesis control system according to claim 7, wherein the neural network is a fuzzy neural network.

17. The prosthesis control system according to claim 7, further comprising a muscle activity sensor, wherein the controller utilizes the limbic-control signals as feedforward signals and muscle activation as recorded by the muscle activity sensor as feedback signals.

18. A fiber optic for transmitting light into the brain through the scalp and past hair, the fiber optic comprising:
an elongated optical fiber body comprising a distal end, a proximal end and elongated fiber body, wherein the proximal end is configured to receive light from a light source and the elongated fiber body is configured to channel light received from the light source at the proximal end to the distal end; and
a bulb coupled with the distal end of the optical fiber, wherein the bulb is configured to transmit light from the elongated fiber optic body into the brain through the scalp and past hair.

19. The fiber optic according to claim 18, wherein the bulb comprises a substantially spherical shape.

20. The fiber optic according to claim 18, wherein the bulb and the optical fiber comprise a continuous first material.

21. A method for training a prosthesis system, wherein the prosthesis system comprises a man-made neural network, a brain imaging system, and a prosthesis, the training utilizing a muscle activity detector, the method comprising:
receiving brain activity data from the brain imaging system;
receiving muscular response data from the muscle activity detector, wherein the muscular response data corresponds with the brain activity; and
training the man-made neural network to produce the muscular response data from the brain activity data.

22. The method according to claim 21, wherein the neural network is a fuzzy neural network.

23. The method according to claim 21, wherein the muscle activity detector comprises an electromyograph.

* * * * *